United States Patent
Thotadakumbri et al.

(10) Patent No.: US 7,493,798 B2
(45) Date of Patent: Feb. 24, 2009

(54) SENSOR FOR DETECTING THE ADULTERATION AND QUALITY OF FLUIDS

(75) Inventors: Raviprakash Thotadakumbri, Hanumanthnagar (IN); James Z T Liu, Hudson, NH (US)

(73) Assignee: Honeywell International Inc., Morristown, NJ (US)

( * ) Notice: Subject to any disclaimer, the term of this patent is extended or adjusted under 35 U.S.C. 154(b) by 429 days.

(21) Appl. No.: 11/274,566

(22) Filed: Nov. 14, 2005

(65) Prior Publication Data

US 2007/0107498 A1 May 17, 2007

(51) Int. Cl.
G01N 11/00 (2006.01)
(52) U.S. Cl. ..................................... 73/53.01
(58) Field of Classification Search ............... 73/290 R, 73/53.01
See application file for complete search history.

(56) References Cited

U.S. PATENT DOCUMENTS

| | | | |
|---|---|---|---|
| 4,258,736 A | 3/1981 | Denbow | |
| 4,516,077 A | 5/1985 | Fenneman et al. | |
| 5,117,146 A | 5/1992 | Martin et al. | 310/313 R |
| 5,155,708 A | 10/1992 | Bedi et al. | 367/152 |
| 5,235,235 A | 8/1993 | Martin et al. | 310/313 D |
| 5,289,073 A | 2/1994 | Mariani | 310/313 D |
| 5,594,327 A | 1/1997 | Sagredos et al. | |
| 5,760,298 A | 6/1998 | Fisher et al. | |
| 5,821,425 A | 10/1998 | Mariani et al. | 73/703 |
| 6,186,005 B1 | 2/2001 | Leidl | |
| 6,293,136 B1 | 9/2001 | Kim | 73/19.03 |
| 6,314,791 B1 | 11/2001 | Rapp et al. | 73/24.06 |

(Continued)

FOREIGN PATENT DOCUMENTS

SU 1465819 A1 3/1989

OTHER PUBLICATIONS

Matsubara Y et al., Observation of Transient Charge Relaxation of Oil Within a Cylindrical Vessel, Industry Applications Society Annual Meeting,Oct. 1993, NY, USA, p. 1704-1708.
Vig, John R. *Dual-Mode Oscillators for Clocks and Sensors*, 1999 IEEE Ultrasonics Symposium J. Nieb, T. Hamacher, P. Schulze Lammers, E. Weber, P. Boeker, *A Miniatureized Thermal Desorption Unit for Chemical Sensing Below Odor Threshold*, Elsevier B.V., Sensors and Actuators B95 (2003) 1-5 J. Z. Liu, Construction Optimization for Acoustic Wave Chemical Sensor Selectivity *Acooustic Wave Technology Sensors*, Sensors Magazine Online, Oct. 2000.

*Primary Examiner*—Daniel S Larkin
*Assistant Examiner*—Rodney T Frank
(74) *Attorney, Agent, or Firm*—Kermit D. Lopez; Luis M. Ortiz

(57) ABSTRACT

A relaxation time constant associated with a fluid can be determined and then compared with a stored reference value. The difference between the relaxation time constant and the stored reference value can then be calculated in order to provide qualitative and/or quantitative data indicative of an adulteration of the fluid. The relaxation time constant associated with the fluid can be determined by first generating a static charge and then injecting the static charge into the fluid. The charge can then be collected from the fluid and utilized to determine the relaxation time constant.

20 Claims, 3 Drawing Sheets

U.S. PATENT DOCUMENTS

| | | | |
|---|---|---|---|
| 6,449,580 B1 * | 9/2002 | Bardetsky et al. | 702/130 |
| 6,568,271 B2 | 5/2003 | Shah et al. | 73/599 |
| 6,571,638 B2 | 6/2003 | Hines et al. | 73/702 |
| 6,640,613 B2 | 11/2003 | Rapp et al. | 73/24.01 |
| 6,693,444 B2 | 2/2004 | Lin et al. | 324/698 |
| 6,781,388 B2 | 8/2004 | Wang et al. | 324/690 |
| 2002/0113521 A1 | 8/2002 | Rapp et al. | 310/313 R |
| 2003/0057968 A1 | 3/2003 | Wang et al. | 324/690 |
| 2003/0076743 A1 | 4/2003 | Thompson et al. | 367/140 |
| 2003/0196477 A1 | 10/2003 | Auner et al. | 73/24.06 |
| 2004/0012399 A1 | 1/2004 | Lin et al. | 324/698 |

\* cited by examiner

SENSOR FOR DETECTING THE ADULTERATION AND QUALITY OF FLUIDS

TECHNICAL FIELD

Embodiments are generally related to sensing devices. Embodiments are also related to the testing of the quality and adulteration of fluids. Embodiments are additionally related to acoustic wave sensors, such as, for example, Surface Acoustic Wave (SAW) and Bulk Acoustic Wave (BAW) sensor devices.

BACKGROUND

Liquid quality sensors are utilized in a number of commercial, agricultural, industrial and consumer applications. The ability to detect the quality and adulteration of a liquid or fluid is important for a number of quality and safety reasons.

Consumers and users come across many types of fluids and liquids in everyday life. For example, fluids, such as milk, edible oil and so forth, are encountered as a matter of daily living. It is expected that such liquids be clean and pure. Due to a lack of awareness or complexity of the any testing of these products, consumers are left with no choice but to accept the material "as is". What is needed to overcome these problems is a simple and reliable technique and/or device for confirming the quality of the material. Similarly the same technology can also be used for other applications in industry such as the detection of adulterated petrochemicals, oil quality in automobile and so forth.

Qualitative testing helps to determine what is present in a given liquid. Quantitative testing provides information on how much of a constituent is present in a given liquid this technology can be used for both qualitative and quantitative testing.

One liquid sensing method for the detection of the adulteration of fuels, for example, relies on the use of markers. Various chemical/biochemical markers are available. The marker is added in trace level with the fuel and whenever the product is tested, the marked chemical is detected and measured by specific instruments. This methodology is limited in practicality and efficiency and is also quite expense to implement. It is also difficult to maintain a constant dosage at low concentrations. Additionally, many of these markers interact with materials and fuel impurities adding to errors in detection quality.

Based on the foregoing, it is believed that an improved liquid sensor apparatus and methodology is required, which can be readily and efficiently implemented. Such an apparatus and methodology is disclosed herein.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved sensor methods and devices.

It is another aspect of the present invention to provide for an improved liquid quality sensor.

It is another aspect of the present invention to provide for a liquid sensor that detects the adulteration of a liquid.

It is a further aspect of the present invention to provide for a liquid sensor that detects the quality and adulteration of a liquid based on an identified relaxation time constant.

It is yet another aspect of the present invention to provide for a liquid sensor that detects the quality and adulteration of a liquid based on one or more detected frequencies associated with the liquid.

The aforementioned aspects of the invention and other objectives and advantages can now be achieved as described herein. A sensor method and system are disclosed. In general, the relaxation time constant associated with a fluid can be determined and then compared with a stored reference value. The difference between the relaxation time constant and the stored reference value can then be calculated in order to provide qualitative and/or quantitative data indicative of an adulteration of the fluid. The relaxation time constant associated with the fluid can be determined by first generating a static charge and then injecting the static charge into the fluid. The charge can then be collected from the fluid and utilized to determine the relaxation time constant.

In accordance with another embodiment, a liquid sensor apparatus can be configured, which is composed of a piezoelectric substrate and a plurality of IDT (Interdigital Transducer) electrodes formed thereon. The piezoelectric substrate and the plurality of IDT electrodes form a liquid sensor apparatus such that the piezoelectric substrate and the plurality of IDT electrodes are exposed to a liquid to provide frequency data indicative of a relaxation time constant associated with the liquid, thereby permitting the relaxation time constant to be utilized as a basis for detecting impurities in the liquid. The liquid sensor apparatus can be provided as an acoustic wave sensor, such as, for example, a Bulk Acoustic Wave (BAW) device. The frequency data provides data indicative of the damping of the liquid. Such damping information provides an indication of the viscosity of the liquid. The generated frequency data can provide multiple-frequency information utilized to detect at least one liquid molecule associated with the liquid based on the relaxation time of one or more of the liquid molecules. The frequency data can comprise, for example, one or more of the following types of frequency information: a fundamental frequency, a $3^{rd}$ overtone, a $5^{th}$ overtone, and so forth.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

The embodiments disclosed herein are based on the fact that all fluids have a specific value of relaxation time constant ($T_r$) in their unadulterated state and under defined conditions. Any adulteration will bring about a change in their relaxation time constant value. Thus, adulteration in fluids can be detected by first determining the $T_r$ value of the test sample, and then comparing it with a stored reference value. Hence by finding the change in the relaxation time constant value of fluids, it is possible to detect the adulteration of such fluids both qualitatively and quantitatively.

Figure 1:
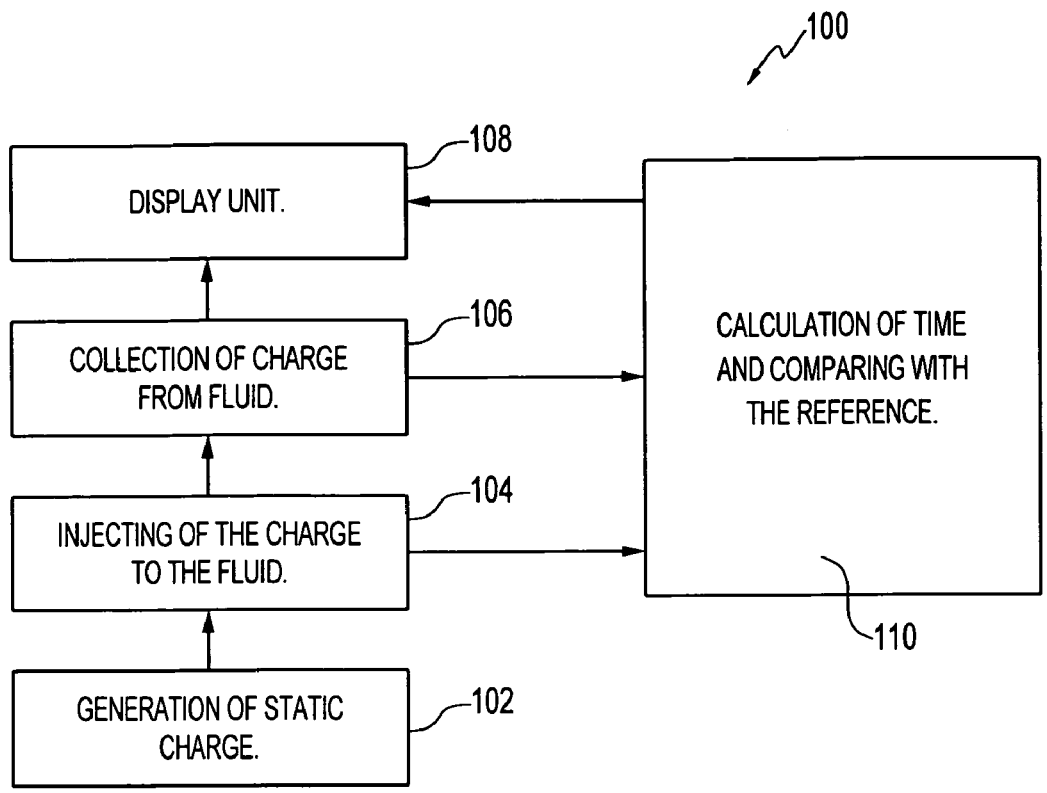
FIG. 1 illustrates a block diagram of a sensor apparatus that can be implemented in accordance with a preferred embodiment.

The innovation described herein with respect to particular embodiments is based on the well know "relaxation time constant" of different material. If some amount of charge is placed inside a volume of a material, the Coulomb forces on the individual charges cause them to migrate away from each other (i.e., assuming the charge is all positive or all negative). The end result is a surface charge on the outer surface of the conductor while the inside of the conductor remains charge-neutral. The time required for the conductor to reach this charge-neutral state is related to a time constant designated as a relaxation time constant. Note that the "Relaxation time constant" of a material is the ratio of its permittivity to conductivity. Since the materials under discussion are insulating in nature hence the constant is quite large, (e.g., in a range of milliseconds to a few seconds), which is sufficient to measure using electronics circuitry. Any addition of impurity or change in quality can increase its permittivity and decrease its conductivity or vice versa, hence there is a considerable change in the relaxation time constant; this change is the measure of adulteration of fluids. In accordance with one embodiment, a sensor can be configured with five parts or functions as indicated in FIG. 1, which illustrates a block diagram of a sensor apparatus 100 that can be implemented in accordance with a preferred embodiment. The apparatus 100 depicted in FIG. 1 is composed of a variety of modules 102, 104, 106, 108 and 110 that represents specific functions and/or devices within apparatus 100. As indicated at module 102, the generation of static charge can occur. Such a static charge can be injected into a fluid, as indicated at module 104. Following processing of the operation depicted at module 104, an operation can be performed as illustrated at module 110, wherein time is calculated and compared with a reference value. Note that the operation described at module 110 involves knowledge of a determination of the $T_r$ value of a test sample, and then comparing it with a stored reference value.

Charge may be collected from the fluid as indicated at module 106 following implementation of the operation illustrated at module 104. Similarly, the operation described at module 110 can be processed following processing of the operation described at module 106, or the operation or component depicted at module 108 can be processed. Module 108 represents a display unit wherein data may be displayed. Data processed as indicated at module 110 can be displayed via the display unit indicated at module 108.

The sensor apparatus 100 is thus composed of five parts, components and or functionalities. The first part, as represented by module 102, involves, the generation of charge. The second part as indicated at module 104, involves the injection of charge in the fluid. The third part of apparatus 100 involves the collection of charge, as indicated by module 106. The fourth part of apparatus 100 involves the measurement of time required to collect the charge as indicated at module 110. The fifth part of apparatus 100 is directed toward the display unit as represented by module 108.

Static charge generated will be injected to the fluid and collected at some point and the time taken for the charge to reach that point is measured and compared with standard reference. Calibrated time will be displayed in terms of its quality/adulteration. Sensor apparatus 100 can be calibrated to any type of fluid and corresponding data can be stored in the memory of a microprocessor, once the relaxation time constant of the material is obtained. The relaxation time constant can then compared with the stored value, as indicated at module 110, and resulting information displayed on a monitor such as that of display unit or display module 108.

Figure 2:
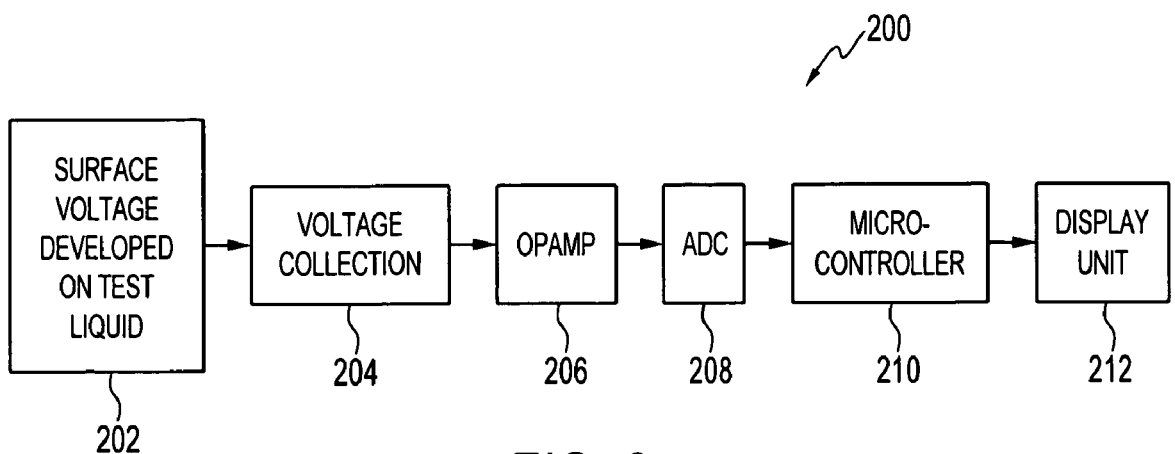
FIG. 2 illustrates a block diagram of a sensor apparatus that can be implemented in accordance with another embodiment.

FIG. 2 illustrates a block diagram of a sensor apparatus 200 that can be implemented in accordance with another embodiment. Note that components and/or functionalities depicted in apparatus 200 are analogous to the components depicted in FIG. 1. For example, module 202 depicted in FIG. 1 indicates that surface voltage is developed on a test liquid. The functionality represented by module 202 is thus analogous to the functionality illustrated at module 102 depicted in FIG. 1. The operation depicted at module 204 with respect to voltage collection is similar to the operation depicted at module 106 in FIG. 1.

FIG. 2 additionally illustrates the use of a component 206, such as, for example, an operational amplifier, a FET or a MOSFET device. Output from the operational amplifier or FET or MOSFET component 206 can be provided to an analog-to-digital converter 208 whose output can then be transferred to a micro-controller 210. Output from the microcontroller 210 is then transmitted to a display unit 212 for display thereon. Display unit 212 depicted in FIG. 2 is analogous to the display unit indicated at module 108 in FIG. 1.

Note that embodiments of the present invention can be implemented in the context of modules, such as, for example, modules 102, 104, 106, 108, 110 and modules 202, 204, 206, 208, 210, 212. Such modules may constitute hardware modules, such as, for example, electronic components of a computer system (e.g., a display unit, microprocessor, etc). Such modules may also constitute software modules. In the computer programming arts, a software module can be implemented as a collection of routines and data structures that performs particular tasks or implements a particular abstract data type.

Software modules generally are composed of two parts. First, a software module may list the constants, data types, variable, routines and the like that can be accessed by other modules or routines. Second, a software module can be configured as an implementation, which can be private (i.e., accessible perhaps only to the module), and that contains the source code that actually implements the routines or subroutines upon which the module is based. The term module, as utilized herein can therefore refer to hardware modules and/or software modules or implementations thereof. Such modules can be utilized separately or together to form a program product that can be implemented through signal-bearing media, including transmission media and recordable media.

Many liquid quality sensors available in the market (e.g., the oil quality sensors in automobiles) make use of the fact that there is a change in the capacitance with a change in quality. The technology described herein, however, with respect to particular embodiments takes into account the change in conductivity. Hence, the embodiments described herein can provide an enhanced resolution for the measurement of the quality.

As an example, consider one of the methods for the detection of adulteration of fuels—the use of markers. Various chemical/biochemical markers are available. The marker is added in trace level with the fuel and whenever the product is to be tested, the marked chemical is detected and measured by specific instruments. But there are quite a few disadvantages with this approach, such as, for example, the relatively high cost involved along with the difficulty in maintaining a constant dosage at low concentrations. Other disadvantages of this approach stem from the fact that markers interact with materials and fuel impurities. The fluid quality sensor described herein, however, is based on an inherent property of the liquid. Hence, the aforementioned problems are overcome, along with present a relatively low cost sensor option.

The embodiments described herein can be applied to a variety of applications. For example, sensor apparatus 100 and/or 200 can be utilized to detect the adulteration of mozzarella cheese (e.g., with bovine milk). Note that Mozzarella cheese is made from water buffalo milk. Usually, the cheese is adulterated with bovine milk. The cheese can thus be melted and its relaxation time constant tested as indicated herein. Another example involves testing of choline chloride adulteration. Choline is a water soluble vitamin. Choline chloride is used as a supplement (e.g. for animals). Usually it is contaminated with inorganic chlorides, hydrochlorides etc. Thus, sensor apparatus 100 and/or 200 can be utilized to test a constructed solution and its relaxation time constant. Other applications include a wide range of clinical tests, detection of chemical salts, therapeutic drug levels, paints and non-fluids, such as, for example, plastics in their molten state.

Figure 3:
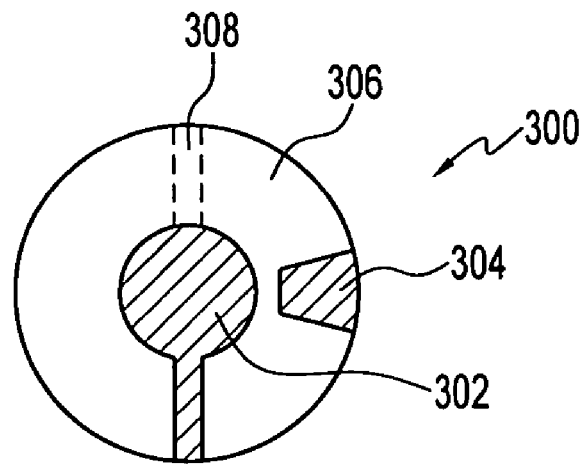
FIG. 3 illustrates a top view of a sensor apparatus that can be implemented in accordance with an alternative embodiment.
Figure 4:
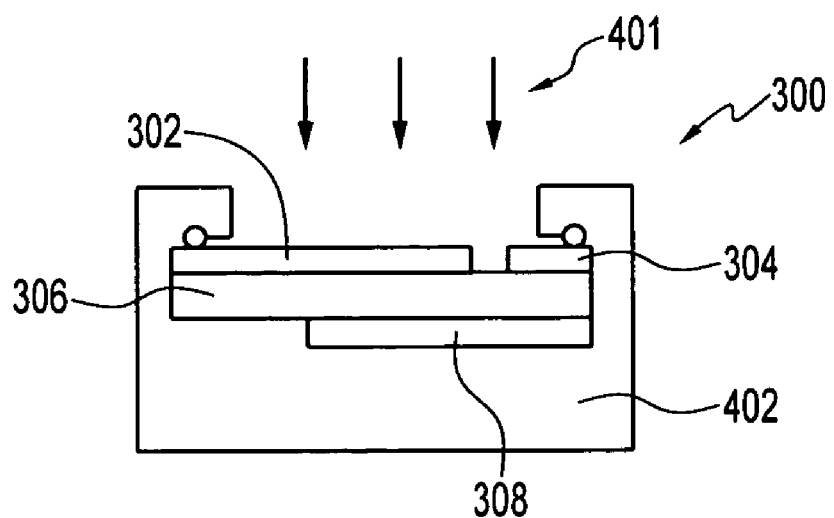
FIG. 4 illustrates a side view of the sensor apparatus depicted in FIG. 3.

FIG. 3 illustrates a top view of a sensor apparatus 300 that can be implemented in accordance with an alternative embodiment. FIG. 4 illustrates a side view of the sensor apparatus 300 depicted in FIG. 3. Sensor apparatus 300 is an alternative version of the sensor apparatus 100, 500 described earlier. Sensor apparatus 300 takes advantage of the fact that conductivity (i.e., through resistance measurement) information can be obtained through the edition of one or more electrodes 302, 304, 308 on a piezoelectric substrate 306 in the context of an acoustic wave device. Sensor apparatus 300 includes the piezoelectric substrate 306 within a sealed chamber 402. Substrate 306 and electrodes 302, 304, 308 formed thereon can be hermetically sealed within the sealed chamber 402.

Arrows 401 depicted in FIG. 4 indicates the direction of liquid exposure to the sensor apparatus 300. The corrosivity of the liquid indicated by arrows 401 can be obtained, for example, through etch rate monitoring by measuring the frequency of the acoustic wave sensor device 300 (i.e., mass loading can change the frequency). Viscosity information about the liquid indicated by arrows 401 can be obtained through oscillation amplitude measurement. The configuration depicted in FIGS. 3-4 thus solves the problem of measuring liquid properties such as viscosity, conductivity, and corrosivity as needed for environmental monitoring (e.g., water pollution), industrial process control, oil quality measurement, and so forth.

Substrate 306 can be formed from one or more types of acoustic wave materials. Among the piezoelectric substrate materials that can be used for implementing substrate 306, the most common are quartz ($SiO_2$), lithium tantalate ($LiTaO_3$) and, to a lesser degree, lithium niobate ($LiNbO_3$). Each has specific advantages and disadvantages, which include cost, temperature dependence, attenuation, and propagation velocity. One property of utilizing quartz for substrate 306 is that it is possible to select the temperature dependence of the material by the cut angle and the wave propagation direction. With proper selection, the first order temperature effect can be minimized. The acoustic wave sensor 300 may be designed by maximizing this effect, depending of course on design goals. This is not true of lithium niobate or lithium tantalate, where linear temperature dependence always exists for all material cuts and propagation directions. Other materials that can be utilized to implement substrate 306 include, but not limited to gallium arsenide (GaAs), silicon carbide (SiC), langasite (LGS), zinc oxide (ZnO), aluminum nitride (AlN), lead zirconium titanate (PZT), and/or polyvinylidene fluoride (PVdF).

Acoustic wave apparatus 300 functions based on the mode of wave propagation through or on the piezoelectric substrate 306. Acoustic waves are distinguished primarily by their velocities and displacement directions; many combinations are possible, depending on the material and boundary conditions. The electrode or Interdigital Transducer (IDT) of sensor 300 provides the electric field necessary to displace the substrate 306 and thus form an acoustic wave. The wave propagates through the substrate 306, where it is converted back to an electric field at an IDT or electrode on the other side. Transverse, or shear, waves have particle displacements that are normal to the direction of wave propagation and which can be polarized so that the particle displacements are either parallel to or normal to the sensing surface. Shear horizontal wave motion signifies transverse displacements polarized parallel to the sensing surface. Shear vertical motion indicates transverse displacements normal to the surface. Each electrode 302, 304, 308 formed on substrate 306 can function as an IDT.

A wave propagating through the substrate 306 constitutes a bulk wave. The most commonly utilize bulk acoustic wave (BAW) devices are the thickness shear mode (TSM) resonator and the shear-horizontal acoustic plate mode (SH-APM) sensor. Thus, sensor 300 can be implemented as a BAW sensor device. If the wave propagates on the surface of the substrate, it is known as a surface wave. The most widely used surface wave devices are the surface acoustic wave sensor and the shear-horizontal surface acoustic wave (SH-SAW) sensor, also known as the surface transverse wave (STW) sensor. Note that the acoustic wave sensor apparatus 300 can be implemented as a Bulk Acoustic Wave (BAW) sensor.

Sensor apparatus 300 can be utilized to obtain the viscosity of a fluid by measuring the damping of the liquid. For liquid applications other than oil (e.g., milk, as indicated earlier), the mass-loading effect (i.e., frequency change) can be utilized to obtain additional information, depending on the quality of the sensing film utilized.

Figure 5:
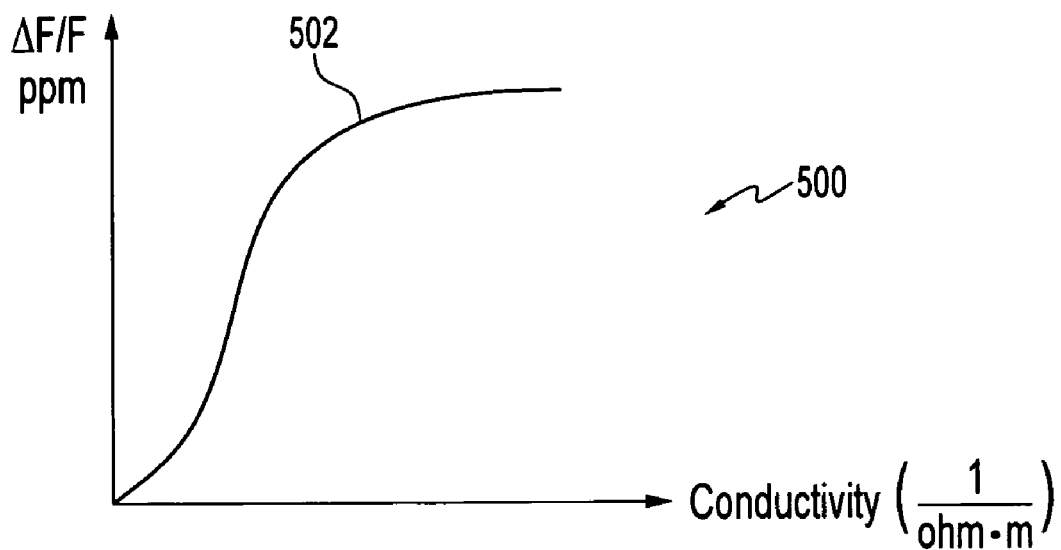
FIG. 5 illustrates a graph depicting a representative sensor response curve in accordance with an alternative embodiment.
Figure 6:
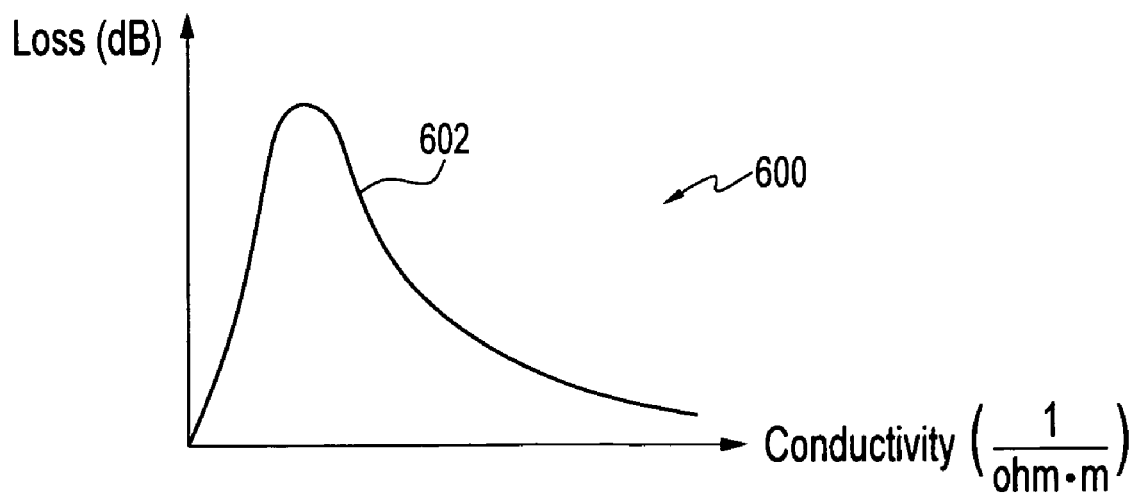
FIG. 6 illustrates a graph depicting a representative sensor response curve that measures a different parameter for the same measurand depicted in FIG. 5, in accordance with an alternative embodiment.

FIG. 5 illustrates a graph 500 depicting a representative sensor response curve 502 in accordance with an alternative embodiment. FIG. 6 illustrates a graph 600 depicting a representative sensor response curve 602 that measures a different parameter for the same measurand depicted in FIG. 5, in accordance with an alternative embodiment. Note that graphs 500 and 600 are associated with apparatus 600 depicted in FIGS. 3-4, depending upon design considerations and applications.

Graphs 500 and 600 demonstrate liquid conductivity variation with acoustic wave sensor frequency change, and liquid conductivity variation with acoustic wave sensor vibration power dissipation. The data generated by graphs 500 and 600 can be generated by considering, for example, an RC time constant associated with the liquid conductivity and the interfacial capacitance (capacitance of the substrate and capacitance of liquid in parallel). The power dissipation, or the loss, peaks at RC=1 and naturally goes to zero as shown in lower figure. The phase shift, or the δF/F, changes more rapidly with conductivity when RC=1 and at slower rate when RC>1.

Liquid impurities can be characterized by different methods, FTIR, HPLC, magnetic resonance, etc. A simpler technique, however, is based on the measurement of the relaxation time constant. When electrodes 302, 304, 308 of the acoustic wave sensor 300 (e.g., as a BAW sensor) are exposed to a liquid, as indicated by arrows 401 in FIG. 4, the application of a DC electric field on a quartz crystal resonator induce a fast variation of the resonance frequency followed by a slow quasi-exponential decal typical of ionic impurity relaxation. The measurement of the relaxation time constant offers the possibility of identifying the nature of liquid impurities. This method is thus based on the diffusion of the impurity ions under a DC field, the frequency shift resulting from the non-linear elastic effect utilized to detect the impurity relaxation. In general, the nature and concentration of the impurity can be deducted from the relaxation time and relaxation amplitude.

Sensor apparatus 300 can function for multiple-frequency detection applications and can sense liquid molecule based on their relaxation time, which is related to the structure rather than mass of the analytes. Sensor apparatus 300 (e.g., a BAW sensor) can be utilized as a multiple frequency sensor, detecting the fundamental frequency, the $3^{rd}$ overtone, the $5^{th}$ overtone, and so forth.

It is contemplated that the use of the present invention can involve components having different characteristics. It is intended that the scope of the present invention be defined by the claims appended hereto, giving full cognizance to equivalents in all respects.

What is claimed is:

1. A sensor method, comprising:
   determining a relaxation time constant associated with a fluid;
   comparing said relaxation time constant with a stored reference value; and
   calculating a difference between said relaxation time constant and said stored reference value in order to provide data indicative of an adulteration of said fluid, wherein said relaxation time constant associated with said fluid is determined by: generating a static charge; injecting said stating charge into said fluid; and collecting said charge from said fluid; and utilizing said static charge collected from said fluid to determine said relaxation time constant.

2. The method of claim 1 wherein said data comprises qualitative information about said adulteration of said fluid.

3. The method of claim 1 wherein data comprises quantitative information about said adulteration of said fluid.

4. A liquid sensor apparatus, comprising:
   a module for determining a relaxation time constant associated with a fluid;
   a module for comparing said relaxation time constant with a stored reference value; and
   a module for calculating a difference between said relaxation time constant and said stored reference value in order to provide data indicative of an adulteration of said fluid; and
   wherein said relaxation time constant associated with said fluid is determined by: generating a static charge; injecting said static charge into said fluid; collecting said charge from said fluid; and utilizing said static charge collected from said fluid to determine said relaxation time constant.

5. The apparatus of claim 4 wherein said data comprises qualitative information about said adulteration of said fluid.

6. The apparatus of claim 4 wherein data comprises quantitative information about said adulteration of said fluid.

7. The apparatus of claim 4 further comprising a module for generating said static charge.

8. The apparatus of claim 4 further comprising a module for injecting said static charge into said fluid.

9. The apparatus of claim 4 further comprising a module for collecting said charge from said fluid.

10. The apparatus of claim 4 further comprising a display unit for displaying data indicative of said adulteration of said fluid.

11. The apparatus of claim 4 further comprising a piezoelectric substrate within a sealed chamber, including a plurality of electrodes formed upon said substrate and located within said sealed chamber to assist in providing said data indicative of said adulteration of said fluid.

12. A liquid sensor apparatus, comprising:
   a module for determining a relaxation time constant associated with a fluid;
   a module for comparing said relaxation time constant with a stored reference value;
   a module for calculating a difference between said relaxation time constant and said stored reference value in order to provide data indicative of an adulteration of said fluid, wherein said relaxation time constant associated with said fluid is determined by: generating a static charge; injecting said static charge into said fluid; collecting said charge from said fluid; and utilizing said static charge collected from said fluid to determine said relaxation time constant; and
   a display unit for displaying data indicative of said adulteration of said fluid.

13. The apparatus of claim 12 wherein said data comprises qualitative information about said adulteration of said fluid.

14. The apparatus of claim 12 wherein data comprises quantitative information about said adulteration of said fluid.

15. The apparatus of claim 13 further comprising a module for generating said static charge.

16. The apparatus of claim 13 further comprising a module for injecting said static charge into said fluid.

17. The apparatus of claim 13 further comprising a module for collecting said charge from said fluid.

18. The apparatus of claim 14 further comprising a module for generating said static charge.

19. The apparatus of claim 14 further comprising a module for injecting said static charge into said fluid.

20. The apparatus of claim 14 further comprising a module for collecting said charge from said fluid.

* * * * *